United States Patent [19]

Blumenthal et al.

[11] Patent Number: 4,731,332

[45] Date of Patent: Mar. 15, 1988

[54] METHOD AND TEST KIT FOR DETERMINING THE AMOUNT OF POLAR SUBSTANCES IN FAT

[75] Inventors: Michael M. Blumenthal, Metuchen, N.J.; Jerry R. Stockler, Wantagh, N.Y.

[73] Assignee: Oil Process Systems, Inc., Allentown, Pa.

[21] Appl. No.: 739,930

[22] Filed: May 31, 1985

Related U.S. Application Data

[63] Continuation-in-part of Ser. No. 621,050, Jun. 15, 1984, abandoned.

[51] Int. Cl.⁴ .................... G01N 21/01; G01N 33/03
[52] U.S. Cl. .......................... 436/61; 422/61; 422/75; 436/60; 436/164; 436/178
[58] Field of Search .............. 422/61, 75; 436/60, 436/61, 163, 164, 178; 356/70, 36

[56] References Cited

U.S. PATENT DOCUMENTS

| | | | |
|---|---|---|---|
| 2,089,017 | 8/1937 | Burk | 436/60 X |
| 2,176,618 | 10/1939 | Wilson | 356/70 |
| 3,121,613 | 2/1964 | Bittner | 436/163 X |
| 3,510,260 | 5/1970 | Krawetz et al. | 436/60 |
| 3,744,907 | 7/1973 | Whelan | 356/70 |
| 4,349,353 | 9/1982 | Blumenthal et al. | 422/61 X |

FOREIGN PATENT DOCUMENTS

| | | | |
|---|---|---|---|
| 2543543 | 4/1977 | Fed. Rep. of Germany | 436/60 |
| 2543544 | 4/1977 | Fed. Rep. of Germany | 436/60 |
| 2630052 | 1/1978 | Fed. Rep. of Germany | 436/60 |
| 52-32396 | 3/1977 | Japan | 436/61 |
| 0065496 | 5/1977 | Japan | 436/61 |

Primary Examiner—David L. Lacey
Assistant Examiner—Timothy M. McMahon
Attorney, Agent, or Firm—Lerner, David, Littenberg, Krumholz & Mentlik

[57] ABSTRACT

A composition and test kit for determining the amount of polar substances in fat are disclosd by employing a test solution which is immiscible with the fat in question, and which provides a polychromatic visible or fluorescent color change in the test solution in response to characteristic amounts of polar substances in the fat. The visible or fluorescent color change can be used to compare to a known standard to determine the amount of polar substances in the fat.

19 Claims, No Drawings

METHOD AND TEST KIT FOR DETERMINING THE AMOUNT OF POLAR SUBSTANCES IN FAT

BACKGROUND OF THE INVENTION

This application is a continuation-in-part of application Ser. No. 621,050 filed on June 15, 1984 and now abandoned.

The present invention relates to a method and test kit for determining the amount of polar substances in fat. More particularly, the invention relates to a method of employing a test solution which is immiscible with fat.

Various methods have been disclosed for determining polar substances in fats, especially oxyacids such as oxidized fatty acids. A number of such methods are disclosed in German Auslegeschrift 25 43 543. In one such method, the conditions of oxidation of a fat is estimated by means of brown coloration resulting from the warming of the fat or oil with alcoholic KOH. In this case, the extinction of the solution is measured against a solution of the original fat.

German Auslegeschrift No. 25 43 543 also refers to German Patentschrift No. 21 50 513 which is said to disclose a process in which the fat in question is shaken at room temperature with a mixture of fat solvents and alcoholic KOH. Thereafter a brown liquid is separated from whose color tone the degree of oxidation of the fat is read. As pointed out in German Auslegeschrift No. 25 43 543, the process of German Patentschrift No. 21 50 513 is lengthy, taking up to an hour.

Still another technique is described in German Auslegeschrift 25 43 543 in which heated deep-frying fats are shaken with alcoholic KOH. After separation of the mixture, the upper layer of the alcoholic-alkali extract is filtered and treated with an indicator solution containing methylene blue and/or 2,6-dichlorophenolindophenol. By virtue of the differences of color, the degree of breakdown of the fat is determined. As pointed out in German Auslegeschrift 25 43 543, this process shows only rather unclear gradation of color and requires also a filtration, so that it is not suitable for rapid determination.

German Auslegeschrift 25 43 543 itself discloses a method in which the base and then the fat to be characterized are added to an alcohol, serving as a fat solvent, and shaken. Then a certain amount of a solution of a indicator in water or in an organic solvent is added and again shaken. After about two minutes, the resulting color in the solution is compared with a color chart. Similar disclosures are also contained in German Offenlegungsschrift 26 30 052, but in addition, bromthymol blue is mentioned as a suitable indicator. The procedure of these publications has a disadvantage in that it produces only one phase from the mixing of the fat to be characterized and the test solution. Moreover, the procedure requires a number of steps, and therefore is relatively complex for field application by non-experienced personnel.

There is also an officially adopted procedure for determining polar components in frying fats by a chromatographic method referred to as the "IUPAC-AOAC Method", *AOAC Official Methods of Analysis*, (1984) pp. 516–517. The polar materials value found by this test is regarded as directly indicative of the quality of the fat for use in frying.

SUMMARY OF THE INVENTION

It has now been found that a very simple and accurate test for determining the amount of polar substances in fats can be performed by mixing a predetermined amount of a one phase test solution with a predetermined amount of the fat. The test solution comprises an indicator and a solvent. The indicator is soluble in the solvent and the fat is substantially immiscible with the solvent. The pH of the test solution is such that the indicator in combination with polar substances extracted from the fat will provide polychromatic visible or fluorescent color changes in the test solution in response to characteristic amounts of polar substances in the fat. The indicator and solvent are present in amounts effective to provide the polychromatic visible or fluorescent color change which depends on the amount of polar substances in the fat. The fat and test solution are allowed to separate into a solvent phase and a fat phase, and the amount of polar substances in the fat is determined from the color developed in the solvent phase by comparing said developed color to a known standard.

The process of the invention is simple and fast, i.e., it requires only mixing a predetermined amount of the test solution with a predetermined amount of the fat, shaking, and waiting a short time for the two phases to separate. The test solution of the invention requires no pre-mixing or post-mixing of reagents by the user. The polychromatic color change in the solvent layer makes it easy to differentiate between the results, i.e., to differentiate for example, between blue, light blue, greenish blue, green and brown. The brown color normally appears with bromocresol green only when the admixture is still unseparated. Thus, the process of the present invention can be performed by even non-skilled persons in the field. The process provides colors that are not immediately fugative and final determinations can be delayed, if necessary.

The advantageous process of the invention also allows the use of a simple test kit in determining the amount of polar substances in fat. In particular, the test kit of the invention comprises a test solution comprising an indicator and a solvent in which the indicator is soluble and with which the fat is substantially immiscible. The pH of the test solution is such that, when the test solution is mixed with fat having such a characteristic amount of polar substances therein, the indicator in combination with polar materials extracted from the fat will provide polychromatic visible or fluorescent color changes in said test solution in response to characteristic amounts of polar substances in the fat. Also, the indicator and solvent are present in amounts effective to provide said polychromatic visible or fluorescent color change which depends on the amount of polar substances in the fat. The test kit also includes a set of colors standardized so that each color of the set corresponds to a color developed when a predetermined amount of fat having a specified amount of polar substances is mixed with a predetermined amount of the test solution.

For convenience, the term "fat" is used in the present specification and claims to refer to fats which are solid at room temperature, to oils which are liquid at room temperature and to any other lipid materials from other sources such as foodstuffs, physiological fluids, and animal and vegetable tissues. The process and test kit are preferably used in testing fresh or used frying oils or fats for polar materials therein as a measure of the fats' suitability for use in frying.

DETAILED DESCRIPTION OF THE INVENTION

The method and test kit in accordance with the present invention employs an indicator such as a dye. The indicator in combination with polar substances extracted from the fat provide the polychromatic visible or fluorescent color change in response to polar substances in the fat. This color change is believed to occur by the extraction of colored polar materials in such a fat which colored polar materials thereby change the color tone of the test solution phase by the result of the mixed colors of the indicator and such colored polar materials. However, we do not wish to be bound completely by such theory since some or all of the indicator may actually act as a redox indicator dye by itself changing color in response to the amount of polar substances in the treated fat. The indicators in any event indicate the oxidative, degradative and/or contaminated state of the fat in question.

The polar materials in the fat sample measured in the process of the invention include, for example, oxidized fatty acids, free fatty acids, polar contaminants added to the fat from the food cooked therein (which can be basic or acidic) and thermal degradation products from the fat which can include polymeric and/or colored polar materials. As noted above, it is the latter materials which are believed to provide the characteristic polychromatic visible or fluorescent color change in the present invention. Specifically, although the colored polar materials have been found to constitute only a small portion of the total polar substances in a used fat at, for example, its "throw-away" point, the colored polar materials are contained in the used fat in proportion to the total polar substances. Thus, when in the process of the invention, the color of the test solution is changed by the colored polar materials extracted from the fat sample, the color change reflects both the amount of the colored polar materials and in many cases the total polar materials in the sample.

Suitable indicators for use in the present invention include dyes such as bromphenol blue, thymol blue, xylenol blue, bromcresol purple, methylene violet, methylene green, methyl orange, methyl red, patent blue, bromthymol blue, bromcresol green, cresolindophenol, triphenolindophenol and thymolindophenol. A preferred indicator dye is bromocresol green. Preferably, the dye is blue in the test solution prior to the mixing with the fat. Such blue color will provide a blue to green to brown type polychromatic color change when the colored polar materials from the fat are extracted into the test solution.

The test solution also includes a solvent in which the indicator such as one of the above dyes is soluble. The solvent is, however, substantially immiscible with the fat. The indicator and solvent should be present in relation to each other in amounts effective to provide the polychromatic visible or fluorescent color change which depends on the amount of polar substances in the fat, i.e., the test solution contains an effective amount of the indicator to provide the desired polychromatic visible or fluorescent color change in response to common characteristic amounts of polar substances in the fat.

Suitable solvents include water miscible organic solvents such as polyols, either alone or in combination with varying amounts of water, depending upon the relative solubility of the fat in the organic solvent. Polyols and an aqueous liquid represent a preferred solvent system. Suitable polyols for use in the present invention include glycerol, ethylene glycol, propylene glycol, polyethylene glycol and polypropylene glycol. Ethylene glycol is a preferred polyol. However, any solvent which provides the characteristics described above would be suitable for use in the present process.

For example, the test solution of the present invention can also include materials such as acetone, methyl ethyl ketone, methylisobutyl ketone and ethyl acetate. The use of polyols with water in the test solution of the invention has been found to provide particularly advantageous results in terms of providing a stable test solution and also good phase separation from the fat to be tested.

The pH of the test solution is such that the desired polychromatic color change will be provided. The pH may be acidic, neutral or basic, but is preferably sufficiently acidic or basic so that the color of the indicator (e.g., dye) will be maintained when the test solution is used to treat the fat sample regardless of acidic or basic components in the fat sample itself. In other words, the pH is such that the dye is in either its acidic or basic color, and the dye itself will not change color in response to acidic or basic materials which are extracted from the fat sample. For example, if bromocresol green is being employed, a pH of about 12 will provide a characteristic blue color for the test solution. Specifically, the pH is adjusted to a value of from about 11 to about 14, more preferably, from about 12 to about 13. The alkaline or acidic materials employed in the pH adjustment can be any material sufficient to provide the desired indicator characteristics. For example, the following alkaline materials can be employed in the test solution of the invention: sodium hydroxide, potassium hydroxide, triethanolamine, and quaternary ammonium bases; while suitable acidic materials include hydrochloric or sulfuric acid.

As noted above, the test solution of the present invention contains an effective amount of the indicator so that, when a predetermined amount of the test solution is mixed with a predetermined amount of the fat, a sufficient color change is obtained in the solvent phase to indicate the relative amount of polar substances in the fat. The concentration of the indicator is selected so as to provide a simple comparison of the color developed in the test solution with a standardized set of colors corresponding to normally expected concentrations of polar substances in the fat. Typically, the solution contains from about 0.0001 to about 0.05 parts by weight of the indicator per 100 parts by weight of the test solution. With bromocresol green a typical desirable range has been found to be about 0.002 parts by weight of this dye per 100 parts by weight of the test solution.

In a preferred embodiment of the invention, an effective amount of the indicator is included in the test solution so that, when a predetermined amount of the test solution is mixed with the predetermined amount of a frying fat containing an amount of polar substances making the fat unsuitable for further cooking use, a sufficient visible color development occurs so that a quick and easy determination can be made to discard such used fat or to treat it to remove such polar substances.

By the terminology "characteristic amount" as used here, we mean ranges of concentration of polar substances that typically occur in the fat sample to be tested such as used cooking fat. The visible color change appears in the solvent phase above or below the fat phase after separation of the fat. Thus, sufficient relative amounts of solvent and indicator are present so as to provide the most clearly distinguishable range of colors corresponding to different characteristic amounts of polar substances in the fat sample.

In most instances, the solvent comprises most of the test solution except for the indicator. However, it should be pointed out that other materials can be present in the test solution, such as foam suppressants, materials to enhance the separation of the fat phase from the solvent phase, materials to suppress solvation of unwanted substances into the solvent phase from the fat, and/or the materials used to adjust the pH of the test solution.

The relative amounts of the test solution and fat employed in the method of the invention depend upon a number of factors, including the concentration of the indicator in the test solution, the expected level of polar substances in the fat to be tested, the indicator itself, i.e., the color it develops in relationship to the amount of polar substances, etc. Typically, the test solution is prepared so that it can be mixed in a simple 1:1 volume relationship with the fat sample so that the typical ranges of polar substances in such a predetermined amount of fat will provide a desired range of colors such that it can be visually determined whether the fat contains an undesirable amount of polar substances and therefore should be discarded, or whether the fat is still suitable for use.

The process of the invention is simple to perform even for relatively inexperienced personnel in, for example, fast food outlets and the like since it only requires mixing a predetermined amount of the test solution with a predetermined amount of the fat sample containing an unknown amount of polar substances therein. The mixing normally takes place in a convenient container such as a closed vessel, e.g., a closed test tube or vial. The fat should be liquid and if it is not, should be made liquid by immersion in, for example, hot water or by any other suitable heating means. The mixture can be merely shaken and then allowed to separate into the solvent phase and the fat phase. The amount of polar substances in the fat can then be determined by simply comparing the color developed in the solvent phase with a known standard, e.g., a set of colors standardized so that each color indicates a specific amount of polar substances in the predetermined amount of fat. The colors could also be compared colorimetrically or spectrophotometrically by techniques well known in the art.

No special conditions other than as discussed above are necessary for performing the present invention. Thus, the process of the invention can be performed at ambient conditions. However, other conditions can be employed so long as they do not unexpectedly change the color development obtained by the relative predetermined amounts of the test solution and fat.

The process of the invention has been found to provide results which correlate very well with the IUPAC-AOAC Method referred to above when employed to test for polar materials in used cooking fats. For example, with a test solution including bromcresol green as the dye and ethylene glycol/water as the solvent system with the pH adjusted to 11–14, a quantitive measure (in terms of ranges) of the polar materials in a sample is provided which repeatedly corresponds to the amount of polar materials therein measured by the standard IUPAC-AOAC Method. Moreover, the process of the invention provides such resuls much quicker and certainly by a much simpler technique than the IUPAC-AOAC Method. Further, a typical "throw-away" point for a used cooking fat is when the fat contains 24–27 percent polar materials as determined by the IUPAC-AOAC Method. The process of the invention has again been shown to indicate in a repeatable manner such a "throw-away" point without the need for the complex and lengthy IUPAC-AOAC Method.

Because of the simplicity of the process of the invention, a test kit can be supplied which merely includes the test solution and a set of standardized colors which can be used to compare the color developed in the solvent phase so as to determine the relative amount of polar substances in the predetermined amount of fat and thereby the fat's relative quality or suitability for use or distribution. The set of standardized colors can be compared, for example, by performing the method of the invention with predetermined amounts of the test solution and a series of fat samples containing known amounts of polar substances. These known amounts are preferably selected to represent typical concentrations of polar substances in used fats and include concentrations which would render the fat unsuitable for use in cooking and frying. The predetermined amounts of such fats containing these known amounts of polar substances are then used in the method of the present invention and the colors corresponding to such known amounts of polar substances are allowed to develop in the solvent phase. These colors in the solvent phase corresponding to known amounts of polar substances can either be used directly for comparison with the test result in accordance with the invention or can be used to prepare a color chart for purposes of such comparison. Thus, by the test kit of the present invention, the relative amount of polar substances in an unknown fat sample can be determined easily, inexpensively and on-site.

The color change in the test solution can also be determined by employing an appropriate fluorescing dye in the test solution and irradiating the test solution phase with ultraviolet light. The change in color in the fluorescence of the test solution phase can be compared to known fluorescent color standards and is thus likewise indicative of the amount of polar substance in the test solution phase.

The test kit of the present invention can also include more than one test solution, e.g., with different indicators. For example, three test solutions corresponding to varying ranges of concentrations of polar substances in a predetermined amount of fat can be employed, representing, for example, high concentrations, intermediate concentrations and low concentrations of polar substances. In this manner, one can focus on a particular range of concentrations of polar substances in the fat.

As noted above, the test kit of the invention can employ any suitable apparatus for performing the mixing and separation. Typically, the process of the invention is performed in test tubes and vials. Polypropylene test tubes with screw caps of polyethylene have been found to be suitable containers for performing the process of the invention. Tall, narrow containers are preferred to observe the color change developed in the solvent phase. If desired, lighting can be employed to pass through the sample to provide a clear indication of the color change, e.g., fluorescent light, incandescent, ultraviolet or sunlight can be employed. Also, a colorimeter or a spectrophotometer can be employed.

The test solution of the invention can be prepared by means conventional in the art. For example, the desired amount of alkaline or acidic substance to provide the desired pH can be dissolved in the solvent, and thereafter the solvent can be mixed with the indicator. If an aqueous liquid is employed, the alkaline or acidic material can be first dissolved in the water and then added to a solution of the indicator in, for example, the polyol component of the solvent.

Typical concentrations of polar substances in used fat depend upon a number of factors, including the type of fat employed, the amount of "makeup" fresh fat added to the used fat, etc. In West Germany, concentrations of polar substances in fat of greater than about 24–27% by weight result in the rejection of the oil for varying purposes.

In a preferred embodiment of the invention, the test solution is comprised of from about 0.0001 to about 0.05 parts by weight of indicator, from about 0.5 to about 10 parts by weight of water, and from about 85 to about 99 parts by weight of polyol, all per 100 parts by weight of the test solution. In another preferred embodiment of the invention, the test solution comprises from about 0.0001 to about 0.05 parts by weight of bromocresol green, from about 0.5 to about 10 parts by weight of water, from about 85 to about 99 parts by weight of ethylene glycol, and a sufficient amount of base to maintain the alkaline color of bromcresol green in the test solution regardless of acidic or basic materials extracted from the fat, all per 100 parts by weight of the test solution. Particularly advantageous results have been obtained by a test solution comprised of the following relative amounts of dye, water, base and ethylene glycol: about 0.02 grams of bromocresol green, about 50 milliliters of water containing 2.35 grams of KOH, with the remainder being ethylene glycol to provide one liter of solution.

The following examples are intended to illustrate, but not to limit, the present invention.

EXAMPLE 1

A test solution is prepared by mixing 2.35 grams potassium hydroxide with 50 milliliters water. Approximately 950 milliliters ethylene glycol is added and stirred. 0.02 grams bromocresol green is added and then sufficient ethylene glycol is added to make 1 liter.

A series of fat samples containing known "oxidized" substance concentration was prepared. Two milliliters of each fat sample was mixed in a vial with 2 milliliters of test solution. The vials were capped and shaken and the phases allowed to separate. A series of samples were obtained with the solvent layer showing a change in color from blue to greenish-blue. The color of the test solution was related to the amount of "oxidized" substances in the fat as measured by the method basically as described in German Auslegeschrift No. 25 43 543 and embodied in the Merck Oxyfrit Test. The results are set forth in Table 1 below.

TABLE 1

| Color of Test Solution Phase | Percent "Oxidized" Substances by the Merck Oxyfrit Test |
| --- | --- |
| Dark Blue | 0.0 |
| Middle Blue | 0.3 |
| Lighter Blue | 0.6 |
| Light Blue | 0.8 |

TABLE 1-continued

| Color of Test Solution Phase | Percent "Oxidized" Substances by the Merck Oxyfrit Test |
| --- | --- |
| Greenish-Blue | 1.0 |

Two milliliters of a fat sample containing an unknown amount of "oxidized" substances is then mixed in the same manner with two milliliters of the test solution. The vial is shaken, the phases allowed to separate, and the color developed in the solvent phase is compared with the colors in the solvent phase from the standardization procedure described above to determine the amount of "oxidized" substance present in the unknown fat sample.

EXAMPLE 2

A series of fats containing varying amounts of polar materials ranging from 0 to 27 percent and above were tested by the IUPAC-AOAC Method referred to above. Samples from the same fats were also tested in accordance with the process of the invention by employing the test solution of the invention as described in Example 1 above and by mixing 2 ml of the test solution with 2 ml of the fat sample as in Example 1. The color developed in the test solution phase in the process of the invention repeatably corresponded to the amounts of the polar materials as measured by the IUPAC-AOAC Method as indicated in Table 2 below:

TABLE 2

| Color of Test Solution Phase | Percent Polar Materials as Measured by IUPAC-AOAC Method |
| --- | --- |
| Blue | 0–12 |
| Light Blue | 12–24 |
| Greenish Blue | 24–27 |
| Green | >27 |

Moreover, this same test solution has been found to consistently mark the same basic "throw-away" point for the used cooking fat as the IUPAC-AOAC Method.

It will be understood that the embodiments described herein are merely exemplary and that a person skilled in the art may make many variations and modifications without departing from the spirit and scope of the invention. All such modifications and variations are intended to be included within the scope of the invention as defined in the appended claims.

We claim:

1. A process for the determination of the amount of polar substances in fat, said process comprising the steps of:

(1) mixing a predetermined amount of a one phase test solution with a predetermined amount of the fat, said test solution including an indicator and a solvent, wherein the indicator is soluble in the solvent and the fat is substantially immiscible with the solvent, wherein the pH of the test solution is sufficiently acidic or basic such that any change in color of said test solution is not due to the presence of acids or bases extracted from said fat into said test solution, and said indicator in combination with polar substances extracted from the fat will provide polychromatic visible or fluorescent color changes in said test solution in response to characteristic amounts of polar substances in the fat, and wherein the indicator and solvent are present in amounts effective to provide said polychromatic visible or fluorescent color change in relation to the amount of polar substances in the fat;

(2) allowing the fat and test solution to separate into a solvent phase and a fat phase; and (3) determining the amount of polar substances in the fat from the color developed in the solvent phase by comparing said developed color to a known standard.

2. A process according to claim 1, wherein said determining step is performed by comparing the color developed in the solvent phase with a set of colors standardized so that each color indicates an amount of polar substances in the predetermined amount of the fat and indicates the fat's quality.

3. A process according to claim 1, wherein the indicator is selected from the group consisting of bromphenol blue, thymol blue, xylenol blue, bromcresol purple, methylene violet, methylene green, methyl orange, methyl red, patent blue, bromthymol blue, bromcresol green, cresolindophenol, triphenolindophenol, thymolindophenol and mixtures thereof.

4. A process according to claim 1, wherein said solvent comprises a water miscible organic solvent and an aqueous liquid.

5. A process according to claim 1, wherein said solvent comprises a polyol organic solvent and an aqueous liquid.

6. A process according to claim 5, wherein said polyol is selected from the group consisting of ethylene glycol, glycerol, propylene glycol, polyethylene glycol, polypropylene glycol and mixtures thereof.

7. A process according to claim 1, wherein the test solution is comprised of an indicator in an amount effective to provide a visible or fluorescent color change when the test solution is mixed with fat having characteristic amounts of polar substances therein, and of water and polyol in proportion to each other so as to extract polar substances from the fat and so as to provide a solvent system immiscible with the fat.

8. A process according to claim 1, wherein the test solution is comprised of from about 0.0001 to about 0.05 parts by weight of indicator per 100 parts by weight of the test solution, from about 0.5 to about 10 parts by weight of water per 100 parts by weight of the test solution, and from about 85 to about 99 parts by weight of polyol per 100 parts by weight of test solution.

9. A process according to claim 1, wherein the test solution is comprised of from about 0.0001 to about 0.05 parts by weight of bromocresol green per 100 parts by weight of the test solution, from about 0.5 to about 10 parts by weight of water per 100 parts by weight of the test solution, from about 85 to about 99 parts by weight of ethylene glycol per 100 parts by weight of test solution and a sufficient amount of base to maintain the alkaline color of bromocresol green in the test solution, regardless of acidic or basic materials extracted from the fat.

10. A process according to claim 1, wherein the test solution is comprised of the following components in the following relative amounts: about 0.02 grams of bromocresol green; about 50 milliliters of water; and about 950 milliliters of ethylene glycol with the remainder being sufficient KOH to adjust the pH to maintain the alkaline color of bromocresol green in the test solution regardless of acidic or basic materials extracted from the fat, all made to a total final volume of about 1 liter.

11. A test kit for determining the amount of polar substances in fat, said test kit comprising (1) a one phase solution including an indicator and a solvent in which the indicator is soluble and with which a fat is substantially immiscible, wherein the pH of the test solution is sufficiently acidic or basic such that any change in color of said test solution is not due to the presence of the extraction of acids or bases extracted from the fat when the test solution is mixed with fat having a characteristic amount of polar substances therein, and the indicator in combination with polar substances to be extracted from the fat will provide a polychromatic visible or fluorescent color change in said test solution in response to such characteristic amounts of polar substances in the fat, and wherein the indicator and solvent are present in amounts effective to provide said polychromatic visible or fluorescent color change in relation to the amount of polar substances in the fat; and (2) a set of colors standardized so that each color of the set corresponds to a color developed when a predetermined amount of fat having a specified amount of polar substances is mixed with a predetermined amount of the test solution.

12. A test kit according to claim 11, wherein the indicator is selected from the group consisting of bromphenol blue, thymol blue, xylenol blue, bromcresol purple, methylene violet, methylene green, methyl orange, methyl red, patent blue, bromthymol blue, bromcresol green, cresolindophenol, triphenolindophenol, thymolindophenol and mixtures thereof.

13. A test kit according to claim 11, wherein said solvent comprises a water miscible organic solvent and an aqueous liquid.

14. A test kit according to claim 11, wherein said solvent comprises a polyol organic solvent and an aqueous liquid.

15. A test kit according to claim 14, wherein said polyol is selected from the group consisting of ethylene glycol, glycerol, propylene glycol, polyethylene glycol, polypropylene glycol and mixtures thereof.

16. A test kit according to claim 11, wherein the test solution is comprised of indicator in an amount effective to provide a visible or fluorescent color change when the test solution is mixed with a fat having a characteristic amount of polar substances therein, and water and polyol in proportion to each other so as to extract the polar substances from the fat and so as to provide a solvent system immiscible with the fat.

17. A test kit according to claim 11, wherein the test solution is comprised of from about 0.0001 to about 0.05 parts by weight of indicator per 100 parts by weight of the test solution, from about 0.5 to about 10 parts by weight of water per 100 parts by weight of the test solution, from about 85 to about 99 parts by weight of polyol per 100 parts by weight of test solution and a sufficient amount of base to maintain the alkaline color of said indicator in the test solution regardless of acidic or basic materials extracted from the fat.

18. A test kit according to claim 11, wherein the test solution is comprised of from about 0.0001 to about 0.05 parts by weight of bromocresol green per 100 parts by weight of the test solution, from about 0.05 to about 10 parts by weight of water per 100 parts by weight of the test solution, and from about 85 to about 99 parts by weight of ethylene glycol per 100 parts by weight of test solution.

19. A test kit according to claim 11, wherein the test solution is comprised of the following components in the following relative amounts: about 0.02 grams of bromocresol green; about 50 milliliters of water; about 950 milliliters of ethylene glycol with the remainder being potassium hydroxide sufficient to adjust the pH to maintain the alkaline color of bromocresol green in the test solution regardless of acidic or basic materials extracted from the fat, made to a total final volume of about 1 liter.

* * * * *